United States Patent [19]
Luhm et al.

[11] Patent Number: 5,602,011
[45] Date of Patent: Feb. 11, 1997

[54] **PURIFIED *THERMOCOCCUS BAROSSII* DNA POLYMERASE**

[75] Inventors: Robert A. Luhm, Mequon, Wis.; Olga B. d'Hennezel; Guy D. Duffaud, both of Raleigh, N.C.; James F. Jolly, Glendale, Wis.; Robert M. Kelly, Cary, N.C.; Eve Y. Ting, Brookfield, Wis.

[73] Assignees: Pharmacia Biotech Inc., Milwaukee, Wis.; North Carolina State University, Raleigh, N.C.

[21] Appl. No.: 375,134

[22] Filed: Jan. 18, 1995

[51] Int. Cl.⁶ .............................. C12N 9/12; C12N 15/54; C12P 19/34
[52] U.S. Cl. .................. 435/91.2; 435/194; 536/23.2
[58] Field of Search .................... 435/194, 91.2; 536/23.2

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.2 |
| 4,889,818 | 12/1989 | Gelfand, et al. | 435/194 |
| 4,965,188 | 10/1990 | Mullis et al. | 435/6 |
| 5,192,674 | 3/1993 | Oshima et al. | 435/194 |
| 5,352,600 | 10/1994 | Gelfand et al. | 435/194 |
| 5,352,778 | 10/1994 | Comb et al. | 536/23.2 |
| 5,413,926 | 5/1995 | Oshima et al. | 435/194 |

OTHER PUBLICATIONS

Uemori et al., Nucleic Acids Research, vol. 21, No. 2, pp. 259–265. 1993.

McPherson et al. "PCR, A Practical Approach", pp. 171–186. 1991.

Olga B. d'Hennezel, "Characterization of a Novel Thermostable DNA Polymerase from a Hydrothermal Submarine Vent Microorganism," North Carolina State University catalogued Apr. 6, 1994.

*Primary Examiner*—Keith D. Hendricks
*Attorney, Agent, or Firm*—Quarles & Brady

[57] ABSTRACT

A preparation of a purified DNA polymerase substantially identical to native DNA polymerase isolated from *Thermococcus barossii* is disclosed. In a preferable form of the present invention, the DNA polymerase is approximately 68 kDa in size, retains at least 90% activity after 8 hours of incubation at 95° C. and retains between 60% and 80% proof-reading ability when catalyzing a polymerization reaction with a primer with a 3 base pair mismatch.

24 Claims, 6 Drawing Sheets

PURIFIED *THERMOCOCCUS BAROSSII* DNA POLYMERASE

FIELD OF THE INVENTION

The present invention relates to a thermostable polymerase isolated from *Thermococcus barossii*. Specifically, the present invention relates to a purified thermostable polymerase with a molecular weight of either approximately 68,000 daltons or approximately 90,000 daltons with enhanced thermostability at 95° C.

BACKGROUND OF THE INVENTION

Thermostable polymerases have been isolated and purified from a number of eubacterial and archaeal (archaebacterial) sources. For example, Comb, et al. U.S. Pat. No. 5,352,778; (Oct. 4, 1994) describes a recombinant thermostable DNA polymerase from *Thermococcus litoralis;* Gelfand, et al. U.S. Pat. No. 5,079,352; (Jan. 7, 1992) discloses a thermostable enzyme purified from *Thermus aquaticus;* PCT WO92/09689 (Mathur, E. J.; published 11 Jun. 1992) describes a thermostable polymerase from *Pyrococcus furiosus*; PCT WO92/03556 (Gelfand, et al., published 5 Mar. 1992) describes a DNA polymerase from *Thermotoga maritima;* and WO92/06202 (Gelfand, et al.; published 16 Apr. 1992) describes a DNA polymerase from *Thermosipho africanus*.

Characteristics and properties such as optima of pH, temperature, degree of thermostability, and ionic requirements have been determined for many of these enzymes. Thermostable polymerases initially found great commercial appeal due to their ability to catalyze polymerization of DNA from a DNA template in the polymerase chain reaction (PCR). Other uses of thermostable polymerase include cycle sequencing of small amounts of DNA, sequencing of PCR products, standard sequencing reactions at elevated temperatures, and reverse transcription PCR type reactions. These techniques have been described in detail. (See, for example, G. A. Hawkins, et al., *Biotechniques* 16:418–20, 1994; M. A. Innis, et al., *Proc. Natl. Acad. Sci. U.S.A.* 85:9436–40, 1988; M. C. Kricker, et al., *Gene* 85:199–204, 1989; J. S. Lee, *DNA Cell Biol.* 10:67–73, 1991; T. W. Myers, et al., *Biochemistry* 30:7661–6, 1991; Wolfe, et al., *Eur. J. Clin. Chem. Clin. Biochem.* 30:717–27, 1992.)

Currently commercially available polymerases suffer from certain limitations when performing the above described procedures. DNA polymerases from *Thermus aquaticus* (Taq) and *Thermus thermophilus* (Tth) lack a sufficient proof-reading function as well as having reduced thermostability. Additionally, long PCR products are difficult to achieve when using Taq and Tth polymerases primarily because of the lack of proof-reading function. DNA prepared using these polymerases frequently requires modification before subsequent manipulations can be performed.

DNA polymerases such as those derived from *Pyrococcus furiosus* and *Thermococcus litoralis* have greater thermostability and exhibit a high degree of proof-reading capability. (See, for example, M. Bergseid, et al., *Strategies in Molecular Biology* 4(3):34–5, 1991; N. F. Cariello, et al., *Nucleic Acids Res.* 19:4193–8, 1991; K. A. Eckert, et al., *PCR Methods and Applications* 1(1):17–24, 1991; H. Kong, et al., *J. Biol. Chem.* 268:1965–75, 1993; T. A. Kunkel, et al., "Fidelity of DNA polymerase used in polymerase chain reactions," *Current Communication in Molecular Biology*, pp. 5–10, 1989; K. S. Lundberg, et al., *Gene* 108:1–6, 1991.) These polymerases, although improvements over the former polymerases, have several drawbacks. Two disadvantages of these polymerases are the higher incubation temperatures to which these polymerases are accustomed as well as an overactive 3' to 5' exonuclease function.

Therefore, it is desirable to develop a thermostable DNA polymerase which functions optimally at approximately 80° C., has increased thermostability, and exhibits proof-reading capabilities that do not overwhelm polymerase function.

SUMMARY OF THE INVENTION

The present invention is a preparation of a purified DNA polymerase substantially identical to native DNA polymerase isolated from *Thermococcus barossii*. In the examples below, we have characterized this DNA polymerase as having two forms, one of which is approximately 90 kDa in size and the other which is approximately 68 kDa in size. We believe that the 68 kDa form is the result of an N-terminal deletion of approximately 186 amino acids from the 90 kDa form.

In an advantageous embodiment of the present invention, the polymerase retains between 60% and 95% of polymerase proof-reading capability when the polymerase catalyzes a polymerization reaction with a primer with a 3 base pair mismatch. Preferably, the polymerase retains between 60% and 80% proof-reading capability. Most preferably, the polymerase retains between 65% and 75% proof-reading capability.

In another advantageous embodiment of the present invention, a preparation a purified DNA polymerase retains between 25% and 60% of polymerase proof-reading capability when the polymerase catalyzes a polymerization reaction with a primer with a 6 base pair mismatch. More preferably, the polymerase retains between 40% and 50% proof-reading capability. Most preferably, the polymerase retains approximately 46% proof-reading capability.

In another advantageous embodiment of the present invention, the polymerase described above retains at least 70% activity after 2 hours of incubation at 95° C. in appropriately buffered solutions. In a preferable embodiment, the polymerase retains at least 80% activity after eight hours of incubation at 95° C. In a more preferable embodiment, the polymerase retains at least 90% activity after 8 hours incubation at 95° C. In a most preferable embodiment, the polymerase retains 100% activity. We refer to the ability to retain enzymatic activity after incubation at 95° C. as "thermostability."

In one embodiment of the present invention, the polymerase is isolated directly from *Thermococcus barossii*. In another embodiment of the present invention, the polymerase is obtained from expression of the DNA sequence encoding the polymerase that has been inserted into a host organism, such as *E. coli*.

The present invention is also a method of elongating or polymerizing a DNA molecule. This method comprises the step of exposing the DNA molecule to a complementary primer molecule, the DNA polymerase of the present invention, and dNTPs under conditions permitting extension of the DNA molecule. The enzyme of the present invention will also be useful in DNA sequencing and polymerase chain reaction (PCR).

It is an object of the present invention to provide a DNA polymerase substantially identical to that isolated from *Thermococcus barossii*.

It is another object of the present invention to provide a DNA polymerase retaining at least 90% activity after 8 hours of incubation at 95° C.

It is another object of the present invention to provide a DNA polymerase with an intermediate proof-reading capability. By "intermediate proof-reading capability," we mean that the polymerase of the present invention has proof-reading capability in a range between that exhibited by exonuclease deficient Taq-like polymerases, exonuclease minus versions of Vent polymerase and Deep Vent polymerase, and polymerases with overactive exonuclease activity such as Vent polymerase, Deep Vent polymerase, and Pfu polymerase.

It is another object of the present invention to provide a polymerase that retains between 60% and 80% of polymerase proof-reading capability when the polymerase catalyzes a polymerization reaction with a primer with a 3 base pair mismatch.

It is another object of the present invention to provide a polymerase that retains between 40% and 50% of polymerase proof-reading capability when the polymerase catalyzes a polymerization reaction with a primer with a 6 base pair mismatch.

It is another object of the present invention to provide a method for elongating a DNA molecule.

It is another object of the present invention to provide a DNA sequence capable of producing the *Thermococcus barossii* DNA polymerase.

Other objects, advantages and features of the present invention will become obvious after examination of the specification, claims and drawings.

DESCRIPTION OF THE INVENTION

The present invention is a preparation of an enzyme having DNA polymerase activity useful for standard sequencing of DNA, polymerase chain reaction, and cycle sequencing. Preferably, this enzyme is thermostable. The thermostable DNA polymerase of this invention is an enzyme which catalyzes the polymerization of DNA that is complementary to the template by the incorporation of deoxyribonucleoside triphosphates from a primer annealed to the template. By "thermostable," we mean an enzyme that has a temperature optima of at least 65° C. Typically these thermostable enzymes retain at least 20% activity after incubation at 95° C. for 4 hours.

This invention provides an improved polymerase with (1) increased thermostability; (2) intermediate proof-reading capability; and (3) greater longevity during extended amplifications. By "intermediate proof-reading capability," we mean that the polymerase of the present invention has a proof-reading capability that is intermediate between thermostable polymerases with a lesser amount of proof-reading ability, such as Taq polymerase, and polymerases with a high amount of proof-reading ability, such as Vent polymerase and Deep Vent polymerase. Also provided is an effective method for the production and purification of said polymerase.

The polymerase of the present invention is substantially identical to a polymerase derived from a previously unclassified strain of microorganism of the genus Thermococcus, identified as *Thermococcus barossii*. By "substantially identical," we mean that the candidate polymerase has at least a 95% amino acid sequence homology and at least 95% of the proof-reading capability and thermostability of native Tba polymerase. A preferable strain of *Thermococcus barossii* was deposited at DSM (Deutsche Sammlung yon Mikroorganismen und Zellkulturen GmbH, Mascheroder Weg 1b, D-38124, Braunschweig, Federal Republic of Germany) on Nov. 1, 1994 at DSM accession number DSM 9535.

In a preferred embodiment, the DNA polymerase is produced directly from *Thermococcus barossii*. The examples below describe a preferable method for isolating the DNA polymerase from *Thermococcus barossii*. The DNA polymerase may also be obtained by expressing a DNA sequence encoding the polymerase in a host organism. Again, the Examples below disclose a preferable method of determining this DNA sequence and a preferable sequence. SEQ ID NO:13 below discloses a preferable partial DNA sequence encoding the 90 kDa form of Tba polymerase. From SEQ ID NO:13, one of skill in the art will be able to isolate probes sufficient to isolate the entire Tba DNA polymerase sequence from a *T. barossii* genomic-library. The Examples below disclose a preferable method for achieving this result. Referring to SEQ ID NO:13, the coding region of the polymerase ranges from initiation at bp 233 to termination at bp 2573. We believe that the 68 kDa form of the enzyme is created by a 186 amino acid deletion at the N-terminal end. Therefore, appropriate deletion (by methods known to those of skill in the art) of the SEQ ID NO:12 coding region will produce a sequence encoding the 68 kDa form of the enzyme.

Once one has obtained a suitable sequence for expressing *Thermococcus barossii* polymerase, this sequence should be combined with appropriate regulatory sequences in a vector, such as a plasmid or virus, designed to promote efficient expression of the sequence in a host organism. One particularly advantageous combination of vector and host organism is a λP$_L$ COL E1 plasmid derivative in a λCI bacterial strain.

Figure 5:
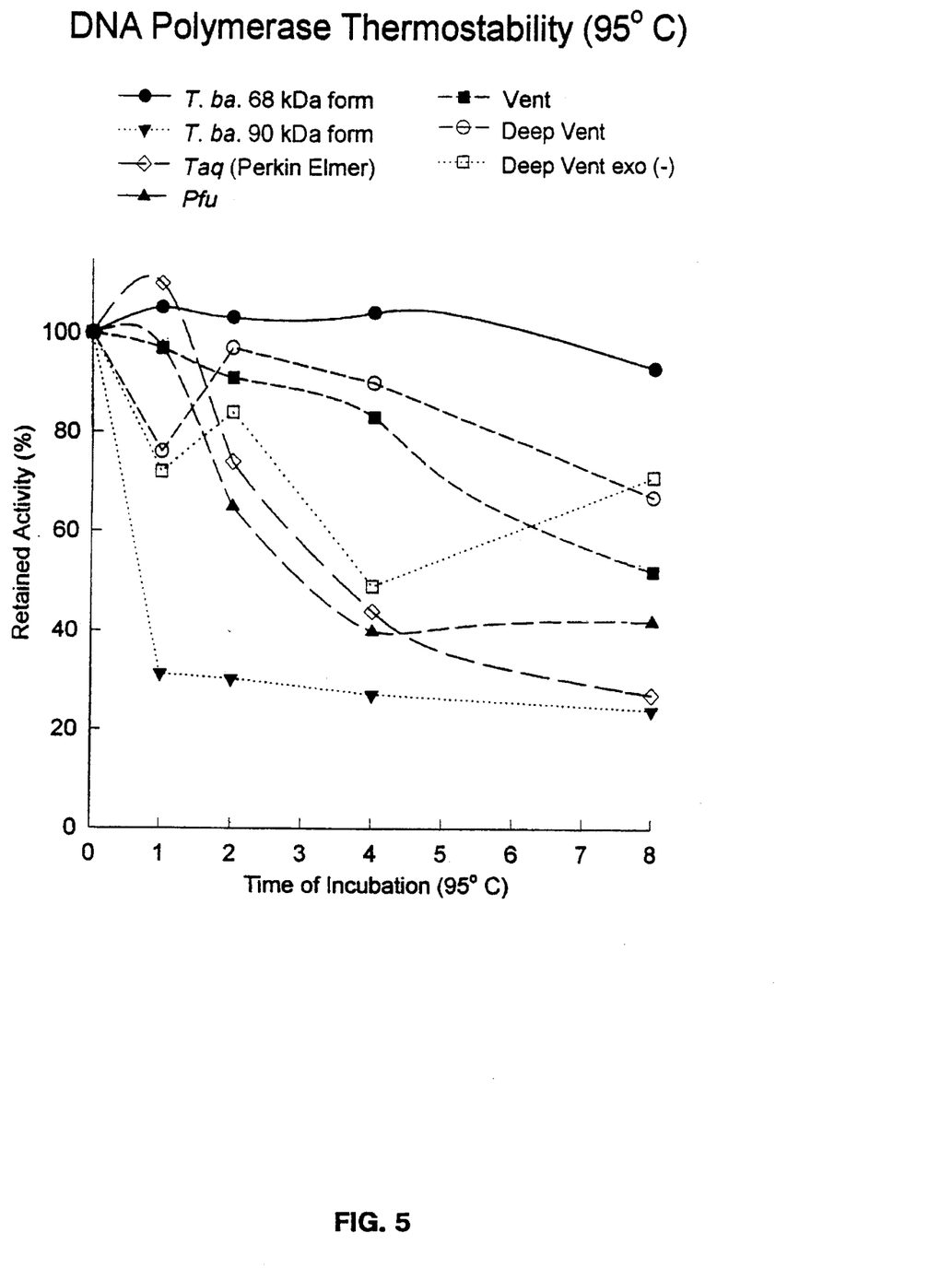
FIG. 5 is a diagram of activity versus incubation time at 95° C. for both the 68 and 90 kDa forms of Tba polymerases, Vent polymerase, Pfu polymerase, Taq polymerase, Deep Vent polymerase and Deep Vent exopolymerase.

It is envisioned that small changes, deletions, and modifications may be made to a DNA sequence isolated from *Thermococcus barossii* that encodes the DNA polymerase. One of skill in the art would know that certain small modifications to the DNA sequence would not impair DNA polymerase activity. The Examples below describe an assay for DNA polymerase ability that would be suitable for a candidate modified sequence. One would simply express a DNA polymerase from the modified sequence and perform the polymerase assay described above. If the candidate molecule performed similarly (at least 95% activity) to the *Thermococcus barossii* polymerase described in the present invention, then the DNA sequence is suitable. One would want to compare the thermostability of the enzyme with that determined for the 90 kDa and 68 kDa forms of *Thermococcus barossii* DNA polymerase. FIG. 5 diagrams a convenient comparative data set. A successful candidate polymerase will have at least 95% of the DNA polymerase thermostability of the 68 kDa form illustrated in FIG. 5 after 8 hours incubation at 95° C.

Figure 6:
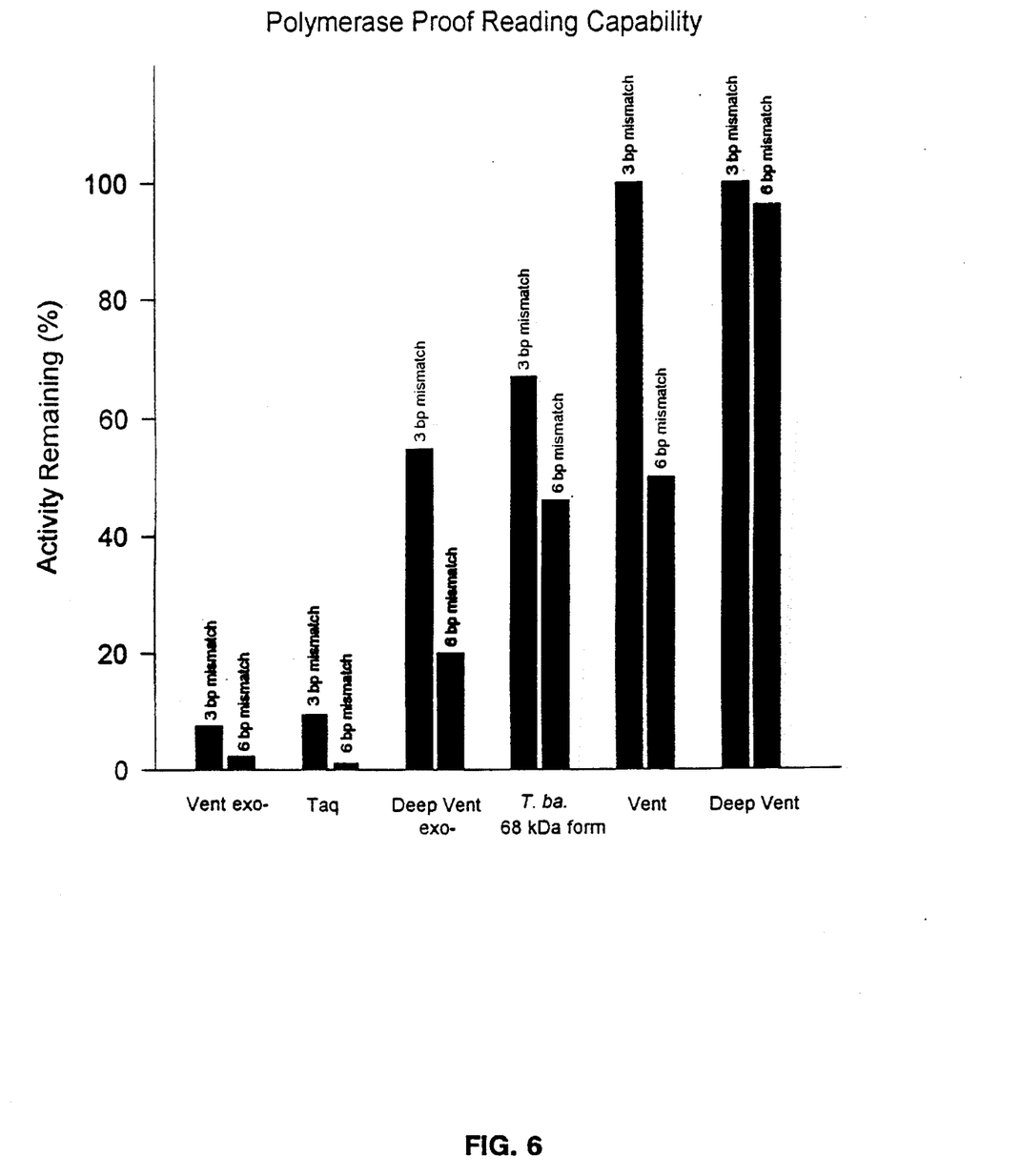
FIG. 6 is a diagram of polymerase proof-reading capability for various thermostable polymerases.

A successful candidate polymerase will also have at least 95% of the proof-reading ability of the 68 kDa form, as described in FIG. 6. The examples below describe a method of determining proof-reading capability.

The polymerase of this invention consists of two distinctively sized entities, both capable of catalyzing the incorporation of nucleoside triphosphates and causing DNA elongation on a single-stranded template. As determined by comparative migration, the molecular weight of the smaller protein migrates between the albumin and phosphorylase b markers on an SDS polyacrylamide gel within a range of 60,000–75,000 daltons. The protein exhibits a half-life of 17–19 hours at 95° C. and retains 100% of its activity when placed at pH 9.3 for 2 hours at 95° C. The approximately 68 kDa protein retains at least 70%, and preferably 90%, of its activity when incubated at 95° C. for 8 hours. We refer to this protein as the "68 kDa form."

As determined by comparative migration, the molecular weight of the large protein migrates near the phosphorylase b marker on an SDS polyacrylamide gel within a range of 86,000–94,000 d. This 90 kDa protein has an optimal pH of approximately 8.5–9.0, an optimal temperature of approximately 70° C.–75° C., requires magnesium ions at an optimal concentration of 5 mM–10 mM, and has an optimal salt concentration of 20 mM–40 mM. We refer to this protein as the "90 kDa form."

The present invention is also a method of elongating a DNA molecule by exposure of a primer to a complementary DNA template, the DNA polymerase of the present invention, and dNTPs under conditions suitable for DNA elongation. Preferably, this method is accomplished as follows: A reaction mixture consisting of reaction buffer (25 mM glycine, pH 9.3, 50 mM KCl, 1 mM DTT); Mg ions at 5–10 mM supplied as $MgCl_2$; and 0.2 mM of each dGTP, dATP, dCTP, and dTTP at pH 9.0 are incubated with the polymerase, template and primer at 72° C. for 2 hours.

EXAMPLES

1. Organism

*T. barossii* was isolated from a deep vent flange, Endeavor Segment, Juan de Fuca Ridge, off the coast of Washington state, U.S.A. As described above, a preferred strain is deposited at DSM at accession number 9535. The organism grows optimally at 82.5° C. but has a temperature range of 60° C.–92° C. Cell densities can reach as high as $4 \times 10^8$ cells/ml in continuous anaerobic culture. The growth conditions allow the addition of NaCl to a level of 15–40 gm/l. Cells have been cultivated in culture pH ranging from 5–8. Other characteristics of this organism are an absolute requirement for elemental sulfur, resistance to the antibiotics streptomycin, chloramphenicol and vancomycin, and a GC percentage of approximately 60.

For our work described below, the organism was cultured in a solution of artificial sea water (ASW). ASW consists of (per liter); NaCl 15–40 g, $MgCl_2 \cdot 6H_2O$ 2 g, KCl 0.7 g, $Na_2SO_4$ 4.0 g; $H_3BO_4$ 0.03 g; KBr 0.01 g; $SrCl_2 \cdot 6H_2O$ 2 mg; $KH_2PO_4$ 0.05 g and $NaHCO_3$ 0.2 g. The ASW solution is supplemented by the addition of 0.05% yeast extract, and 0.25% tryptone. After sterilization, 3 g of a commercially obtained mixture of maltooligosaccaride is added (Pfanstiehl Laboratories, Waukegan, Ill.). We also added 0.003 g of $Na_2WO_4 \cdot 2 H_2O$ and 0.59 g of $CaCl_2 \cdot 2H_2O$. Elemental sulfur (J. T. Baker Chemical Co., Phillipsburg, N.J.) was included in all cultures in the form of powder (5–10 g/l).

The sterilized media, supplemented with the solutions described above and elemental-sulfur, was dispensed in 100 ml culture bottles. Anaerobic conditions were obtained by heating the medium to 98° C., sparging with pre-purified nitrogen (Ultra High Purity (99.999%), National Specialty Gases, Durham, N.C.) and adding 0.375 g $Na_2S \cdot 9 H_2O$ per liter of medium. Resazurin (1 mg/l) was used as a redox indicator. Once the medium had turned clear (anaerobic conditions), the bottles were sealed and inoculated to a cell density of no more than $1 \times 10^6$ cells/ml. The organism was grown in continuous culture until the proper amount of biomass was achieved.

2. Extraction and purification of the DNA Polymerase

The DNA polymerase from *Thermococcus barossii* was extracted and purified by precipitation with polyethylenimine, followed by chromatography on Q sepharose, Heparin Sepharose, Phosophocellulose, and Mono-Q respectively. All procedures were performed at 4° C.

Fifty grams of cells were suspended in 170 ml of a buffer consisting of 50 mM Tris HCl pH 8.0, 5 mM $Na_2EDTA$, 1M KCl, 1 mM DTT and 1 mM PMSF (phenylmethylsulfonyl fluoride). The cell suspension was sonicated to break open the cells. Polyethylenimine to a final concentration of 0.4% was added to the resultant suspension to precipitate the nucleic acids and cell debris. The lysate was centrifuged for 30 minutes at 10,000 RPM and 4° C. Following centrifugation, 75% saturation of ammonium sulfate was added to the supernatant and the protein was precipitated. The suspension was centrifuged at 10,000 RPM in a JA-10 rotor (Beckman) to produce a pellet. The pellet was resuspended in 80 ml of Q Sepharose buffer A (consisting of 50 mM Tris HCl, pH 8.0, 1 mM $Na_2EDTA$, 1 mM DTT and 1 mM PMSF), so that the conductivity of Fraction A was equal to that of the Q Sepharose Buffer A.

Fraction A was applied onto a Q Sepharose column (2.5×15.0 cm, Pharmacia). The column was washed and the enzyme was eluted with Q sepharose Buffer (50 mM Tris HCl pH 8.0, 1 mM $Na_2EDTA$, 100 mM KCl and 1 mM PMSF). The fractions collected were assayed for DNA polymerase activity. Those exhibiting polymerase activity were pooled and given the designation fraction B.

Fraction B was then applied to a Heparin Sepharose column (1.25×16.0 cm, Pharmacia) and washed with the same Q Sepharose buffer. The enzyme was eluted with a linear salt gradient from 0.1M to 0.7M KCl in Q Sepharose buffer. The polymerase activity was assayed and the active fractions with no detectable nuclease(s) were pooled as Fraction C.

Fraction C was dialyzed overnight in phosphocellulose buffer (20 mM $KPO_4$, pH 7.5, 0.5 mM $Na_2EDTA$, 50 mM KCl, 1 mM DTT, 5% glycerol, 0.1% NP-40, and 0.1% Tween 20). The dialysate was applied onto a phosphocellulose p-11 column (1.25×8.0 cm, Whatman) equilibrated with the same buffer. The column was washed with the phosphocellulose buffer and the enzyme was eluted with a linear salt gradient from 50 mM to 500 mM KCl. The activity was assayed and the active fractions with undetectable nuclease(s) were pooled as Fraction D.

Fraction D was dialyzed overnight against a buffer of 20 mM Tris-HCl, pH 8.0, 1 mM $Na_2EDTA$, 1 mM DTT, 50 mM KCl, 5% glycerol, 0.1% NP-40, and 0.1% Tween 20. The dialysate was applied to a 1.0 ml Mono-Q column (Pharmacia) equilibrated and washed with the above described buffer. The enzyme was eluted with a linear salt gradient from 50 mM to 300 mM KCl in the same buffer. Each fraction containing polymerase activity was run on a Phast Gel 8%–25% gradient (Pharmacia) and stained with coomassie brilliant blue. Certain fractions showed a single band in the range of 60,000–75,000 d. This band has been identified as a truncated form of full-length Tba DNA polymerase. Other fractions showed this band as well as a major band in the range 85,000 to 98,000 d as determined by comparative migration relative to molecular weight standards. These bands consist of the truncated form as well as the full-length version of Tba DNA polymerase.

The molecular weight standards employed were the low molecular SDS gel makers (Pharmacia). This marker consists of 6 proteins as follows: Phosphorylase b (94,000 d), Albumin (67,000 d), Ovalbumin (43,000 d), Carbonic anhydrase (30,000 d), Trypsin inhibitor (20,100 d), and α lactalbumin (14,400 d).

3. DNA Polymerase Assay

Assay Mixture:

25 mM Glycine, pH 9.3 (25° C.)

2 mM Magnesium Chloride 50 mM Potassium Chloride 1 mM DTT 0.2 mM dCTP, dGTP, and dTTP 0.1 mM α $^{32}$P-dATP 5.0 µg BSA 1.0 µg M13mp18 ssDNA 0.3 µg single strand primer 5 µl of the enzyme pool containing 1.25 U in dilution buffer was added to 45 µl of the assay mixture described above. 1.25 U of the other commercially available polymerases were diluted in the same dilution buffer and treated similarly. The commercially available polymerases we used in the Examples below were Vent (*Thermococcus litoralis,* available from New England BioLabs, Beverly, Mass.); Taq (*Thermus aquaticus,* available from Perkin Elmer); Pfu (*Pyrococcus furiosus,* available from Stratagene, La Jolla, Calif.) and Deep Vent and Deep Vent exo⁻ (both Pyrococcus species GB-D obtained from New England BioLabs Inc., Beverly, Mass.).

Following gentle mixing, the reaction was incubated at 72° C. for 10 minutes. 50 µl of RNA coprecipitant and 1 ml of cold 10% TCA were added. The suspension was well mixed and incubated on ice for at least 10 minutes, but no longer than 30 minutes. After filtration through glass fiber filters (Whatman), the samples were measured by liquid scintillation counting (Packard Tricarb 2000 CA). In this manner, the quantity of $^{32}$P labeled dATP incorporated into the acid-soluble fraction was calculated. The assay was used in the Examples below to determine DNA polymerase ability.

4. Optimal pH

Figure 1:
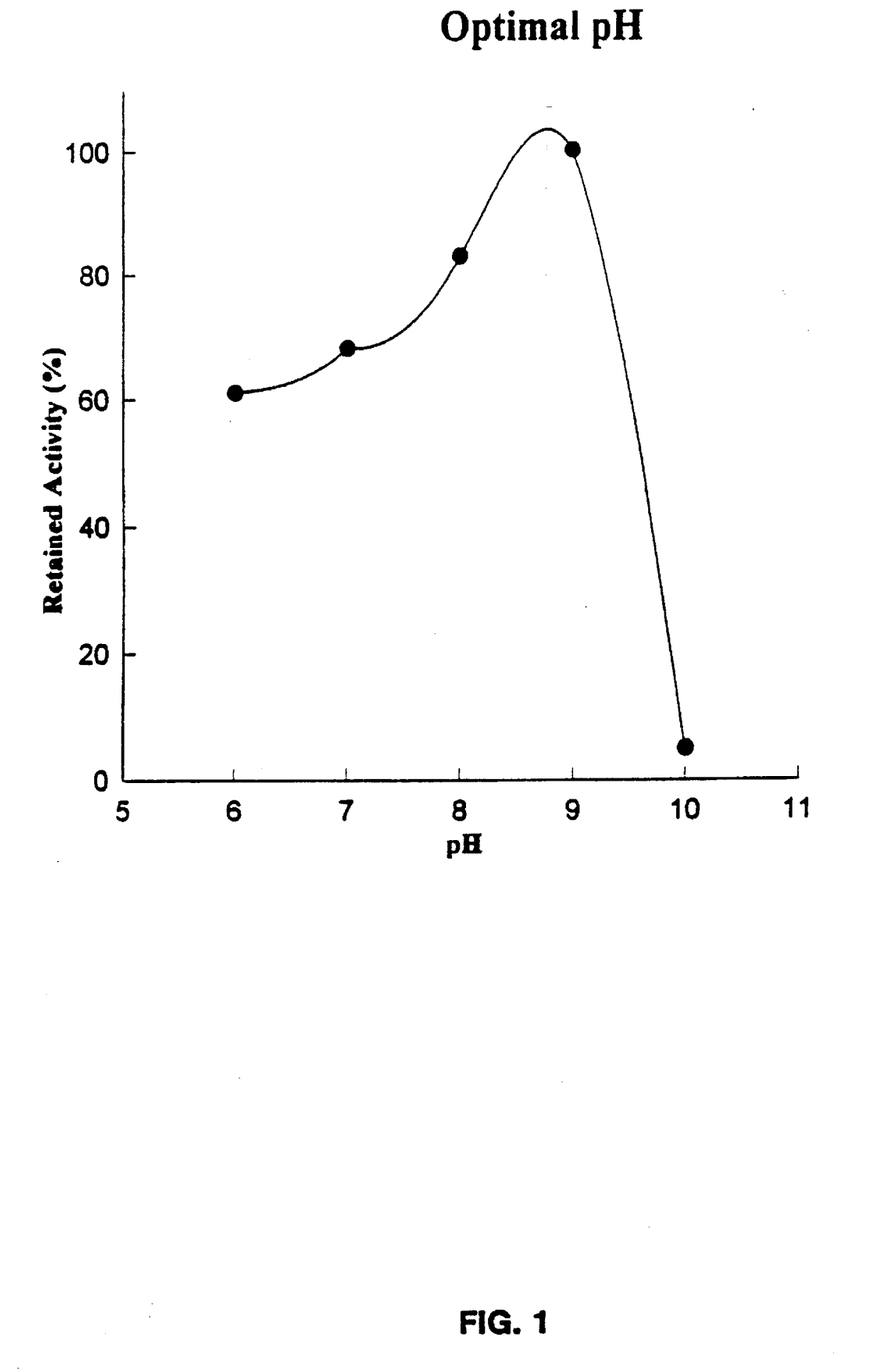
FIG. 1 is a diagram of percentage activity versus pH for the 90 kDa form of Tba polymerase.

The effect of reaction pH on the 90 kDa form of Tba polymerase was examined using the assay buffer. Assay buffer (see supra in Examples) was made at the following pH; 6.0, 7.0, 8.0, 9.3, and 10.5. Aliquots of the diluted polymerases were incubated for 10 minutes at 72° C. in assay buffers representing each pH. Polymerase activity was assayed under standard conditions with only the pH of the assay buffer being altered. The optimal pH of the 90 kDa form of Tba DNA polymerase was approximately 8.5 to 9. The results of measuring activity at various pH values are as shown in FIG. 1. The optimal pH is approximately from 8.5 to 9.0.

5. Optimal MgCl$_2$ Concentration

Figure 2:
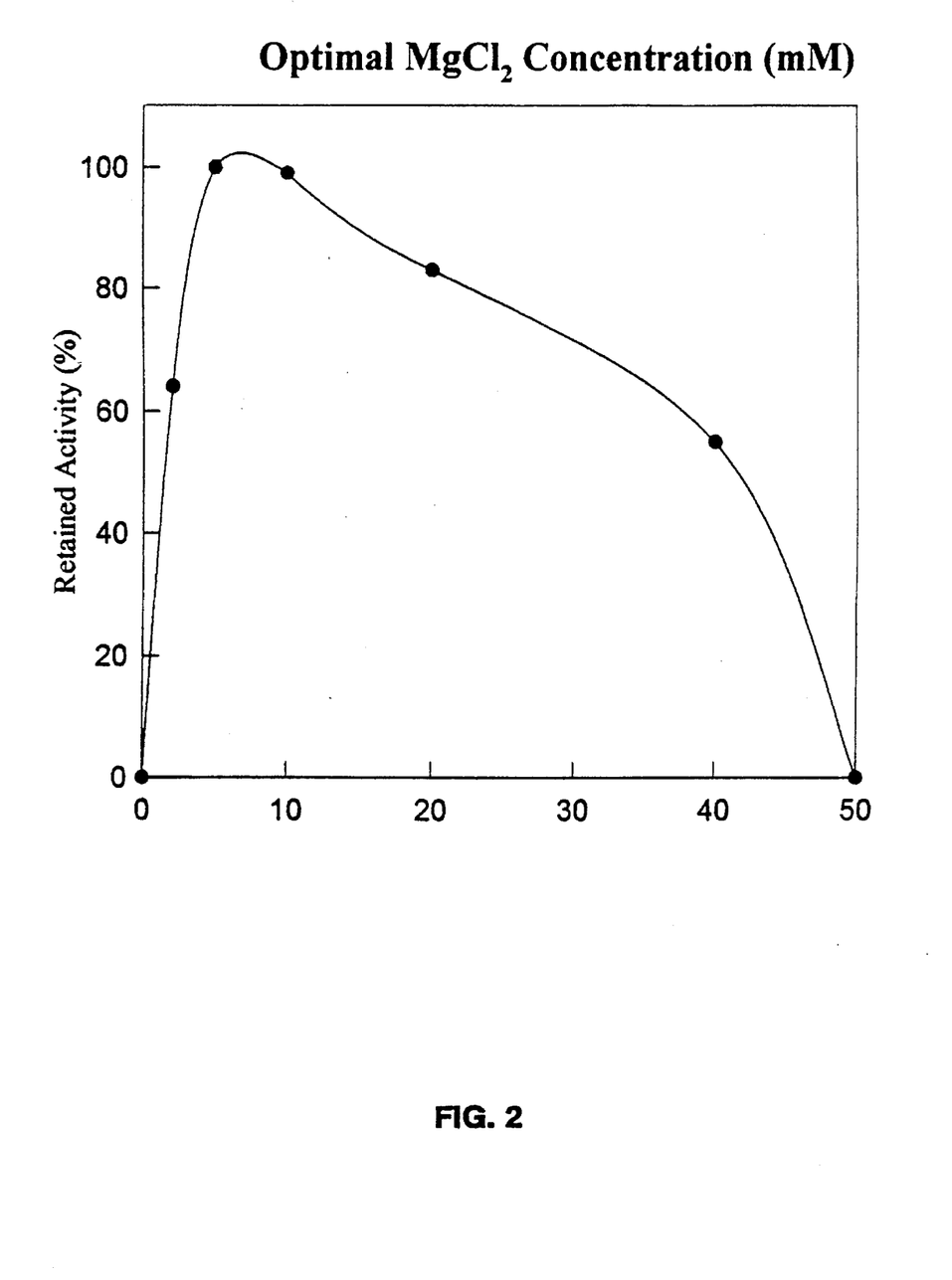
FIG. 2 is a diagram of percentage activity versus MgCl$_2$ concentration for the 90 kDa form of Tba polymerase.

The magnesium chloride concentration of the assay mixture used for measuring the activity of the 90 kDa form of the enzyme was varied, while the other conditions were maintained unchanged. The results are shown, in FIG. 2. An optimal MgCl$_2$ concentration is between 5 and 10 mM.

6. Optimal KCl Concentration

Figure 3:
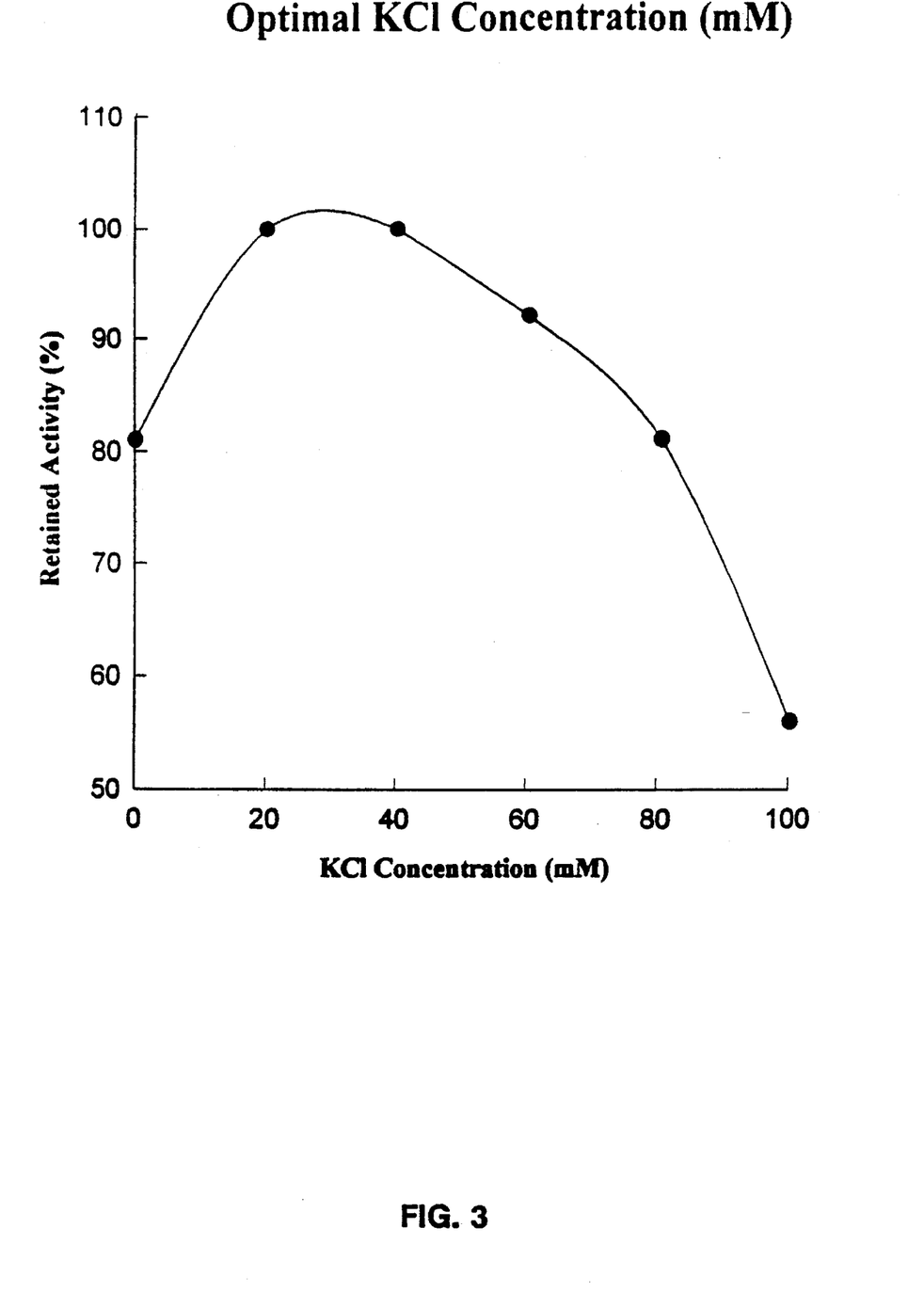
FIG. 3 is a diagram of percentage activity versus KCl concentration of the 90 kDa form of Tba polymerase.

The effect of potassium chloride concentration on the enzymatic activity was measured as described above for MgCl$_2$. The results are shown in FIG. 3. The optimal KCl concentration for the 90 kDa form of the DNA polymerase is between 20 and 40 mM.

7. Optimal Temperature

Figure 4:
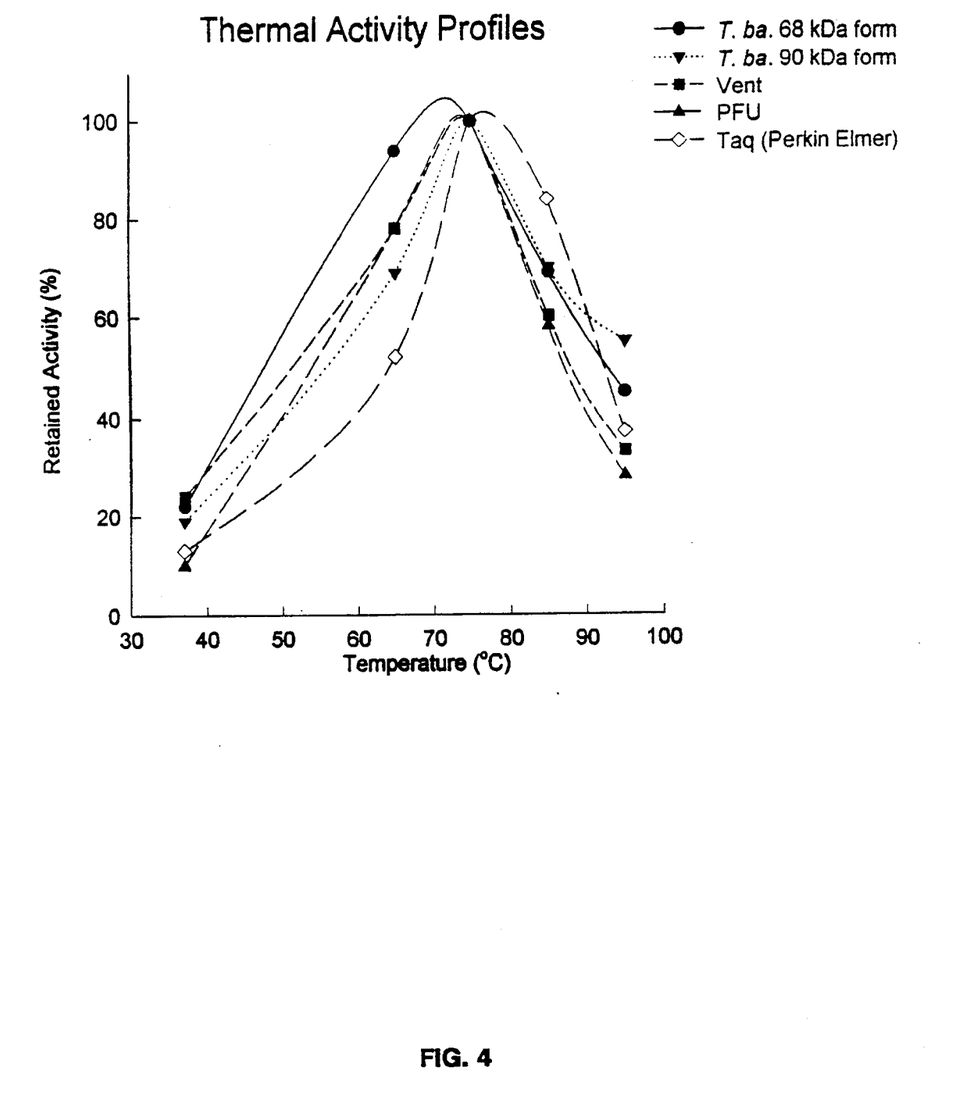
FIG. 4 is a diagram of percentage activity versus temperature for both the 68 and 90 kDa forms of Tba polymerases, Vent polymerase, Pfu polymerase, and Taq polymerase.

The results of measuring enzymatic activity at various temperature are shown in FIG. 4. Both the 68 kDa and 90 kDa form of the polymerase are compared to other commercially available enzymes. The commercially available thermostable polymerases we analyzed were Vent polymerase, Pfu polymerase, and Taq polymerases.

The enzymes were diluted in a dilution buffer consisting of the following components:

50 mM Tris-HCl (pH 7.6)

100 mM NaCl 0.1 mM EDTA 1 mM DTT

1% (v/v) Tween-20 (Bio-Rad)

1% (v/v) NP-40 (Calbiochem)

50% Glycerol

The effect of temperature on each polymerase was assayed utilizing assay conditions described above. 1.25 units in 5 µl dilution buffer was added to 45 µl assay buffer. Aliquots from each polymerase-containing reaction were placed at 37° C., 65° C., 75° C., 85° C., and 95° C. and incubated for 10 minutes. The amount of activity exhibited was determined by the percent of labeled nucleotide incorporated when performing a standard activity assay.

FIG. 4 demonstrates that the optimal temperature for all enzymes is between 70° C. and 75° C.

8. Thermostability Comparison of Different. DNA Polymerases

About 25 units of both the 68 kDa and 90 kDa enzymes and other commercially available thermostable DNA polymerases were diluted to a final volume of 100 ul. The enzymes were diluted in the dilution buffer described above.

The diluted polymerases were incubated for 8 hours at 95° C. At 0, 1, 2, 4, and 8 hour time points, 5 µl aliquots of each DNA polymerase solution were assayed for polymerase activity at 72° C. under standard conditions. The results are shown in FIG. 5. The 68 kDa form of Tba polymerase is the most thermostable, having a half-life of 17 hours at 95° C., while the Vent polymerase has a half-life of only 8 hours [J. Bio. Chem. 268:1965–75 (1993)]. The 90 kDa Tba enzyme is the least thermostable of the test polymerases. This finding might be due to contaminants in the 90 kDa preparation. (The half life value for the 68 kDa form of Tba polymerase was determined from data not presented in FIG. 5. The DNA polymerase thermostability data was determined from experiments with time intervals out to 24 hours.)

9. Molecular Weight

The molecular weights of the two polymerase forms measured by 8%–25% SDS Phast gel electrophoresis were approximately 68,000 daltons and 90,000 daltons, respectively.

10. Exonuclease Activity

The exonuclease activity of Tba enzyme is summarized in Table 1 and diagrammed in FIG. 6. We examined the different polymerases for the ability to correct synthesis errors by determining whether a primer with various mismatches can be extended from a template. The retention of high polymerization activity is indicative of the strength of the 3' to 5' exonuclease.

Three primers were employed—RL-150 (SEQ ID NO:9), RL-151 (SEQ ID NO:10), and RL-152 (SEQ ID NO:11). RL-150 is a 29 bp oligonucleotide that has complete homology to M13mp18 (+) strand. The sequence of RL-150 is as follows:

CGC CAG GGT TTT CCC AGT CAC GAC GTT GT

Sequences RL-151 and RL-152 are 32 bp and 35 bp oligonucleotides respectively. The oligonucleotides are identical to RL-150 for the first 29 bp. RL-151 differs from RL-150 in that it incorporates 3 bp of mismatch on the 3' end of the oligonucleotide. RL-152 incorporates 6 bp of mismatch on the 3' end. These sequences are as follows:

CGC CAG GGT TTT CCC AGT CAC GAC GTT GTT TT RL-151

CGC CAG GGT TTT CCC AGT CAC GAC GTT GTT TTT TT RL-152

The percent incorporation shown in Table 1 is determined relative to the values obtained using RL-150 in a standard polymerase assay. Due to the lack of complete annealing on the 3' end of the duplex when using oligos RL-151 and RL-152 in a polymerase reaction, exonuclease deficient polymerases would not be able to catalyze polymerization of nascent DNA from the primer-template duplex. This would be manifested as little or no incorporation of nucleotide relative to the results obtained using RL-150. Polymerases that possess 3' to 5' exonuclease function would be capable of removing the 3' mismatches and thus continue polymerization. The greater the exonuclease activity, the more mismatched bases removed. Those polymerases with a great deal of exonuclease function would exhibit values equivalent to RL-150 when employing RL-151 and RL-152. As exonuclease function decreased, the results relative to RL-150 would decrease as the number of mismatches increased.

TABLE 1

| DNA Polymerase | % Activity Remaining | |
|---|---|---|
| | RL 151* | RL 152** |
| Vent exo⁻ | 7.6 | 2.3 |
| Taq | 9.7 | 1.3 |
| Deep Vent exo⁻ | 55 | 20 |
| 68 kDa form of Tba enzyme | 67 | 46 |
| Vent | 100 | 50 |
| Deep Vent | 100 | 96 |

*29 basepair oligo + 3 mismatches at the 3' terminus
29 basepair oligo + 6 mismatches at the 3' terminus The results listed in Table 1 and FIG. 6 indicate that significant levels of intermediate exonuclease activity for the 68 kDa form of the Tba DNA polymerase, which falls between the high exonuclease capability of Deep Vent and Vent and the low exonuclease ability of Deep Vent exo⁻, Vent exo⁻ and Taq. The results determined with the 3 base pair mismatch were intermediate between the low exonuclease ability of Deep Vent exo⁻, Vent exo⁻ and Taq (55% or less) and the high exonuclease capability of Deep Vent and Vent polymerase (100%). The proof-reading ability of 68 kDa form of Tba polymerase with a 6 base pair mismatch primer is intermediate between the low exonuclease ability of Deep Vent exo⁻, Taq, and Vent exo⁻ (less than 20%) and the high exonuclease capability of Deep Vent (at least 96%). The proof-reading ability is similar to that obtained with Vent polymerase. However, Vent polymerase is not as thermostable after incubation at 95° C. as the 68 kDa form of Tba polymerase (see FIG. 5**).

11. Purification of DNA from culture

A quantity of Tba cell culture, sufficient to produce a pellet of 1.0 g wet weight, was centrifuged and the resultant cell pellet was resuspended in 4.0 ml 50 mM glucose, 10 mM EDTA (pH 8.0) and 25 mM Tris . HCl (pH 8.0). 600 µl of 8 mg/ml lysozyme in 0.25 mM EDTA was added. The tube was incubated with gentle shaking at 37° C. for 1 hour. 200 µl 20% Sodium dodecyl sulfate was added and incubation was continued for 30 minutes without additional shaking. 160 µl of a solution of 1 mg/ml RNase A was added with incubation at 37° C. for 15 minutes. Finally, 320 µl of Proteinase K (10 mg/ml) was added and the suspension was incubated for an additional 30 minutes at 37° C.

The DNA was extracted several times with Phenol, followed by phenol:chloroform, followed by chloroform alone, with intervening centrifugation at 6000×g, until there was no further interface. The suspension was centrifuged at 6,000×g for 30 minutes in order to separated the phases. The supernatant was transferred to clean sterile tubes. One tenth volume of 3M sodium acetate (pH 5.2) was added and the DNA was precipitated by addition of 2 volumes of ice cold ethanol. The phases were not allowed to mix. The DNA was spooled by disturbing the interface with a glass micropipette. The spooled DNA was transferred to 400 µl of TE.

12. Screening for the presence of the polymerase gene

Degenerate primers were made to potentially related thermostable polymerases. The primers sequences were obtained by looking for regions of consensus between known polymerases. In our particular case, these primers were derived from regions exhibiting a high degree of homology between Vent polymerase and Pfu polymerase. Homologies were determined by performing a direct comparison between Vent polymerase and Pfu polymerase utilizing the DNAsis program produced by Hitachi software. Where differences in the nucleotide sequences of Vent and Pfu existed, degeneracies were built into the primers providing for any combination of codons that would code for that amino acid. Two primers were chosen as potential PCR primers. Primer 1 (RL-155) was CTCAT(ACT)GA-CAA(AG)GGC(CT)T(AG)AT(ACT)CCNATG GAGGG and primer2 (RL-156) was TGCTTCATANACNGCCTC-NAGNGT (AG)TANGTTGG. (Primer 1 is described below at SEQ ID NO:1 and primer 2 is described at SEQ ID NO:2.) The nucleotides in parenthesis or represented by N denote degeneracy. These primers were used to perform standard polymerase chain reaction (PCR) according to the manufacturer's direction Perkin Elmer Cetus). The product of the reactions was purified on low melting point agarose (Sea-Plaque, FMC) using the gelase protocol (Epicentre). The purified DNA fragment was cloned into pUC18 SmaI/Bap utilizing the SureClone PCR cloning kit (Pharmacia). The insert was sequenced using T7 in a modified Sanger chain termination procedure.

Sequence confirmed this fragment as a fragment of a polymerase gene due to sequence similarity with other known polymerases. Other degenerate primers were constructed in an attempt to "walk" further out on the gene utilizing sequence similarity. Two other overlapping fragments of the gene were obtained using the following degenerate primers: Primer 3 (RL-205) CGGATGAT(AT)(CT) T(GA)GA(CT)N NNGATTACATAAC(AT)(AG)AAG A(AT)GG and primer 4 (RL-206) AATGC C(CT)TTGTC(GT)ATGAG(AG)TA(TA)C (GT)CTT(GT) GCAAA(GT)GG as one pair and primer 5 (RL-211) CCCGCGCATAAGGCGCACCATAAACCTCCC and primer 6 (RL-212) CCCCANGCNGTAACGCT(CT) TCAGCACA(CT)TCC as the other pair. (Primers 3–6 are described below in SEQ ID NOs: 3–6, respectively.) These regions were amplified by PCR and purified, cloned, and sequenced as previously described. The entirety of the three overlapping fragments was sequenced in both directions.

A library from *T. barossii* was prepared by partial digestion of genomic DNA with Sau3A I. This was done in order to obtain those portions of the gene not obtainable by the previous method. Pilot digestions were performed to establish the proper amounts of enzyme per unit of time. The established conditions were used to digest 400 μg of genomic DNA. Once digested, the DNA was phenol:chloroform extracted and precipitated. The resultant pellet was resuspended in 400 μl of TE (pH 8.0) and fractionated over a 10%–40% sucrose step gradient.

DNA was banded by centrifugation in an SW-28 rotor (Beckman) at 26,000 RPM for 24 hours at 4° C. The DNA was recovered from the tube by needle puncture at the bottom of the tube. 500 μl fractions were collected and every third fraction was examined for DNA size. Fractions containing DNA of a size ranging from 6,000 bp to 15,000 bp were pooled and dialyzed overnight against three changes of TE (pH 8.0). The dialysate was removed and one tenth volume of 3M sodium acetate (pH 5.2) was added. The DNA was precipitated by the addition of 2 volumes of ice cold ethanol. The well-mixed suspension was incubated for 30 m at −70° C. in a tube suitable for the SW-28 rotor. The DNA was pelleted by centrifugation for 1 hour at 23,000 RPM and 4° C. The purified DNA was allowed to dry following decanting of the ethanol. The dry DNA pellet was resuspended in 400 μl of TE (pH 8.0).

The DNA obtained was ligated to pUC 18 BamHI/Bap and transformed into DH10B competent cells (Life Technologies) in order to produce a library. The resultant library was screened for the presence of positive clones by sequential pool reduction using PCR and two primers internal to the originally amplified overlapping DNA polymerase fragments. These two primers were primer 7 (RL-217) GGTTCATCTTCCTCTTTATCTTCTGCC and primer 8 (RL-218) GGA AGAAGATCGACCTGCCCTACGTCG. (Primers 7 and 8 are described below in SEQ ID NOs:7 and 8.) By this method, a large number of clones were screened with increasingly reduced numbers remaining in the pool. The original screening, which resulted in several positive signals, has since been reduced in pool numbers from 6,000 clones, to 400 clones, to several pools of 24 clones. The final 24 clone pools were screened and individual clones representing the entire gene were isolated as requested.

SEQ ID NO:13 is the DNA sequence generated from the PCR product produced from the degenerated primers. The PCR products were subcloned into pUC18 and double stranded sequencing was performed using a modified Sanger Chain termination method. The protein sequence was the direct translation of the nucleotide sequence (SEQ ID NO:12) using DNAsis software. Referring to SEQ ID NO:13, the coding region of the polymerase ranges from initiation at bp 233 to termination at bp 2573.

We claim:

1. A preparation of purified DNA polymerase native to *Thermococcus barossii*.

2. The preparation of claim 1 wherein the polymerase is approximately 90 kDa.

3. The preparation of claim 1 wherein the polymerase is approximately 68 kDa.

4. The preparation of claim 1 wherein the polymerase is present in both an approximately 90 kDa and approximately 68 kDa form.

5. The preparation of claim 3 wherein the polymerase retains at least 70% activity after eight hours of incubation at 95° C.

6. The preparation of claim 5 wherein the polymerase retains at least 80% activity after eight hours of incubation at 95° C.

7. The preparation of claim 5 wherein the polymerase retains at least 90% activity after eight hours of incubation at 95° C.

8. The preparation of claim 1 wherein the polymerase is isolated from *Thermococcus barossii*.

9. The preparation of claim 1 wherein the polymerase is obtained from expression of a DNA sequence encoding the *Thermococcus barossii* polymerase wherein the DNA sequence is inserted into a host organism other than *Thermococcus barossii*.

10. A preparation of a purified DNA polymerase native to *Thermococcus barossii* wherein the polymerase retains between 60% and 95% of polymerase proof-reading capability when the polymerase catalyzes a polymerization reaction with a primer with a 3 bp mismatch.

11. The preparation of claim 10 wherein the polymerase is thermostable.

12. The preparation of claim 10 wherein the polymerase retains between 60% and 80% proof-reading capability.

13. The preparation of claim 10 wherein the polymerase retains between 65% and 75% proof-reading capability.

14. The preparation of claim 10 wherein the polymerase retains at least 70% activity after eight hours of incubation at 95° C.

15. The preparation of claim 14 wherein the polymerase retains at least 80% activity after eight hours of incubation at 95° C.

16. The preparation of claim 15 wherein the polymerase retains at least 90% activity after eight hours of incubation at 95° C.

17. The preparation of claim 16 wherein the polymerase retains approximately 100% activity after eight hours of incubation at 95° C.

18. The preparation of claim 13 wherein the polymerase retains at least 90% activity after eight hours of incubation at 95° C.

19. A preparation of a purified DNA polymerase native to *Thermococcus barossii* wherein between 25% and 60% of polymerase proof-reading capability is retained when the polymerase catalyzes a polymerization reaction with a primer with a 6 bp mismatch.

20. The preparation of claim 19 wherein between 40% and 50% of the proof-reading capability is retained.

21. A method of elongating a DNA molecule comprising the step of exposing the DNA molecule to a complementary primer molecule, the DNA polymerase of claim 1 and dNTPs under conditions permitting extension of the DNA molecule.

22. A DNA construct comprising a region encoding a DNA polymerase native to *Thermococcus barossii*.

23. The construct of claim 22 wherein the encoding region comprises SEQ ID NO:13.

24. The construct of claim 22 wherein the encoding region comprises a portion of SEQ ID NO:13 sufficient to produce the 68 kDa form of the polymerase.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear     ( i i ) MOLECULE TYPE: oligonucleotide     ( x i ) SEQUENCE DESCRIPTION: SEQ ID NO:1:

CTCATHGACA ARGGCYTRAT HCCNATGGAG GG    32

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear     ( i i ) MOLECULE TYPE: oligonucleotide     ( x i ) SEQUENCE DESCRIPTION: SEQ ID NO:2:

TGCTTCATAN ACNGCCTCNA GNGTRTANGT TGG    33

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear     ( i i ) MOLECULE TYPE: oligonucleotide     ( x i ) SEQUENCE DESCRIPTION: SEQ ID NO:3:

CGGATGATWY TRGAYNNNGA TTACATAACW RAAGAWGG     38

( 2 ) INFORMATION FOR SEQ ID NO:4:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( i i ) MOLECULE TYPE: oligonucleotide     ( x i ) SEQUENCE DESCRIPTION: SEQ ID NO:4:

AATGCCYTTG TCKATGAGRT AWCKCTTKGC AAAKGG     36

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear     ( i i ) MOLECULE TYPE: oligonucleotide     ( x i ) SEQUENCE DESCRIPTION: SEQ ID NO:5:

CCCGCGCATA AGGCGCACCA TAAACCTCCC     30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear     ( i i ) MOLECULE TYPE: oligonucleotide     ( x i ) SEQUENCE DESCRIPTION: SEQ ID NO:6:

CCCCANGCNG TAACGCTYTC AGCACAYTCC     30

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear     ( i i ) MOLECULE TYPE: oligonucleotide     ( x i ) SEQUENCE DESCRIPTION: SEQ ID NO:7:

GGTTCATCTT CCTCTTTATC TTCTGCC     27

( 2 ) INFORMATION FOR SEQ ID NO:8:

( i ) SEQUENCE CHARACTERISTICS:
        ( A ) LENGTH: 27 base pairs (B) TYPE: nucleic acid
    (C) STRANDEDNESS: single
    (D) TOPOLOGY: linear (ii) MOLECULE TYPE: oligonucleotide (xi) SEQUENCE DESCRIPTION: SEQ ID NO:8:

GGAAGAAGAT CGACCTGCCC TACGTCG					27

(2) INFORMATION FOR SEQ ID NO:9:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ii) MOLECULE TYPE: oligonucleotide (xi) SEQUENCE DESCRIPTION: SEQ ID NO:9:

CGCCAGGGTT TTCCCAGTCA CGACGTTGT					29

(2) INFORMATION FOR SEQ ID NO:10:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: oligonucleotide (xi) SEQUENCE DESCRIPTION: SEQ ID NO:10:

CGCCAGGGTT TTCCCAGTCA CGACGTTGTT TT					32

(2) INFORMATION FOR SEQ ID NO:11:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ii) MOLECULE TYPE: oligonucleotide (xi) SEQUENCE DESCRIPTION: SEQ ID NO:11:

CGCCAGGGTT TTCCCAGTCA CGACGTTGTT TTTTT					35

(2) INFORMATION FOR SEQ ID NO:12:

(i) SEQUENCE CHARACTERISTICS:
    (A) LENGTH: 779 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:12:

Met Ile Leu Asp Val Asp Tyr Ile Thr Glu Asp Gly Lys Pro Val Ile
 1               5                  10                  15

Arg Val Phe Lys Lys Asp Lys Gly Glu Phe Lys Ile Glu Tyr Asp Arg
                20                  25                  30

Glu Phe Glu Pro Tyr Ile Tyr Ala Leu Leu Arg Asp Asp Ser Ala Ile
            35                  40                  45

Glu Glu Ile Glu Lys Ile Thr Ala Glu Arg His Gly Lys Val Val Lys
        50                  55                  60

-continued

| Val | Lys | Arg | Ala | Glu | Lys | Val | Lys | Lys | Lys | Phe | Leu | Gly | Arg | Ser | Val |
| 65 | | | | 70 | | | | | 75 | | | | | | 80 |

Glu Val Trp Val Leu Tyr Phe Thr His Pro Gln Asp Val Pro Ala Ile
                    85                  90                  95

Arg Pro Asp Lys Ile Arg Lys His Pro Ala Val Ile Asp Ile Tyr Glu
                100                 105                 110

Tyr Asp Ile Pro Phe Ala Lys Arg Tyr Leu Ile Asp Lys Gly Leu Ile
            115                 120                 125

Pro Met Glu Gly Asp Glu Glu Leu Lys Leu Met Ser Phe Asp Ile Glu
    130                 135                 140

Thr Leu Tyr His Glu Gly Glu Glu Phe Gly Thr Gly Pro Ile Leu Met
145                 150                 155                 160

Ile Ser Tyr Ala Asp Glu Ser Glu Ala Arg Val Ile Thr Trp Lys Lys
                165                 170                 175

Ile Asp Leu Pro Tyr Val Asp Val Val Ser Thr Glu Lys Glu Met Ile
            180                 185                 190

Lys Arg Phe Leu Lys Val Val Lys Glu Lys Asp Pro Asp Val Leu Ile
        195                 200                 205

Thr Tyr Asp Gly Asp Asn Phe Asp Phe Ala Tyr Leu Lys Lys Arg Cys
    210                 215                 220

Glu Lys Leu Gly Val Ser Phe Thr Leu Gly Arg Asp Gly Ser Glu Pro
225                 230                 235                 240

Lys Ile Gln Arg Met Gly Asp Arg Phe Ala Val Glu Val Lys Gly Arg
            245                 250                 255

Ile His Phe Asp Leu Tyr Pro Ala Ile Arg Arg Thr Ile Asn Leu Pro
        260                 265                 270

Thr Tyr Thr Leu Glu Ala Val Tyr Glu Ala Val Phe Gly Lys Pro Lys
    275                 280                 285

Glu Lys Val Tyr Ala Glu Glu Ile Ala Thr Ala Trp Glu Thr Gly Glu
    290                 295                 300

Gly Leu Glu Gly Val Ala Arg Tyr Ser Met Glu Asp Ala Arg Val Thr
305                 310                 315                 320

Tyr Glu Leu Gly Arg Glu Phe Phe Pro Met Glu Ala Gln Leu Ser Arg
            325                 330                 335

Leu Ile Gly Gln Gly Leu Trp Asp Val Ser Arg Ser Ser Thr Gly Asn
        340                 345                 350

Leu Val Glu Trp Phe Leu Leu Arg Lys Ala Tyr Glu Arg Asn Glu Leu
        355                 360                 365

Ala Pro Asn Lys Pro Asp Glu Arg Glu Leu Ala Arg Arg Gly Gly
    370                 375                 380

Tyr Ala Gly Gly Tyr Val Lys Glu Pro Glu Arg Gly Leu Trp Asp Asn
385                 390                 395                 400

Ile Val Tyr Leu Asp Phe Arg Ser Leu Tyr Pro Ser Ile Ile Ile Thr
            405                 410                 415

His Asn Val Ser Pro Asp Thr Leu Asn Arg Glu Gly Cys Lys Ser Tyr
            420                 425                 430

Asp Val Ala Pro Gln Val Gly His Lys Phe Cys Lys Asp Phe Pro Gly
        435                 440                 445

Phe Ile Pro Ser Leu Leu Gly Asn Leu Leu Glu Glu Arg Gln Lys Ile
    450                 455                 460

Lys Arg Lys Met Lys Ala Thr Leu Asp Pro Leu Glu Arg Lys Leu Leu
465                 470                 475                 480

Asp Tyr Arg Gln Arg Ala Ile Lys Ile Leu Ala Asn Ser Phe Tyr Gly
            485                 490                 495

|     |     |     |     |     |     |     |     |     |     |     |     |     |     |
| --- | --- | --- | --- | --- | --- | --- | --- | --- | --- | --- | --- | --- | --- |
| Tyr | Tyr | Gly | Tyr<br>500 | Ala | Arg | Ala | Arg | Trp<br>505 | Tyr | Cys | Lys | Glu<br>510 | Cys | Ala | Glu |
| Ser | Val | Thr<br>515 | Ala | Trp | Gly | Arg | Glu<br>520 | Tyr | Ile | Glu | Met | Val<br>525 | Ile | Arg | Glu |
| Leu | Glu<br>530 | Glu | Lys | Phe | Gly<br>535 | Phe | Lys | Asp | Leu | Tyr | Ala<br>540 | Asp | Thr | Asp | Gly |
| Leu<br>545 | His | Ala | Thr | Ile | Pro<br>550 | Gly | Ala | Asp | Arg | Glu<br>555 | Thr | Val | Lys | Lys | Lys<br>560 |
| Asp | Leu | Glu | Phe | Leu<br>565 | Asn | Tyr | Ile | Asn | Pro<br>570 | Lys | Leu | Pro | Gly | Leu<br>575 | Leu |
| Glu | Leu | Glu | Tyr<br>580 | Glu | Gly | Phe | Tyr | Ser<br>585 | Arg | Gly | Phe | Phe | Val<br>590 | Thr | Lys |
| Lys | Lys | Tyr<br>595 | Ala | Val | Ile | Asp | Glu<br>600 | Glu | Gly | Lys | Ile | Thr<br>605 | Thr | Arg | Gly |
| Leu | Glu<br>610 | Ile | Val | Arg | Arg | Asp<br>615 | Trp | Ser | Glu | Ile | Ala<br>620 | Lys | Glu | Thr | Leu |
| Ala<br>625 | Arg | Val | Leu | Glu | Ala<br>630 | Ile | Leu | Arg | His | Gly<br>635 | Asp | Val | Glu | Glu | Ala<br>640 |
| Val | Arg | Ile | Val | Lys<br>645 | Glu | Glu | Thr | Glu | Lys<br>650 | Leu | Ser | Lys | Tyr | Glu<br>655 | Val |
| Pro | Pro | Glu | Lys<br>660 | Leu | Val | Ile | Thr | Glu<br>665 | Gln | Ile | Thr | Arg | Glu<br>670 | Leu | Lys |
| Asp | Tyr | Lys<br>675 | Ala | Thr | Gly | Pro | His<br>680 | Val | Ala | Ile | Ala | Lys<br>685 | Arg | Leu | Ala |
| Ala | Arg<br>690 | Gly | Ile | Lys | Ile | Arg<br>695 | Pro | Gly | Thr | Val | Ile<br>700 | Ser | Tyr | Ile | Val |
| Leu<br>705 | Lys | Gly | Ser | Gly | Arg<br>710 | Ile | Gly | Asp | Arg | Ala<br>715 | Ile | Pro | Phe | Asp | Glu<br>720 |
| Phe | Asp | Pro | Thr | Lys<br>725 | His | Arg | Tyr | Asp | Ala<br>730 | Asp | Tyr | Tyr | Ile | Glu<br>735 | Asn |
| Gln | Val | Leu | Pro<br>740 | Ala | Val | Glu | Arg | Ile<br>745 | Leu | Arg | Ala | Phe | Gly<br>750 | Tyr | Lys |
| Lys | Glu | Asp<br>755 | Glu | Arg | Tyr | Gln | Lys<br>760 | Thr | Arg | Gln | Val | Gly<br>765 | Leu | Gly | Ala |
| Trp | Leu<br>770 | Gly | Met | Gly | Gly | Glu<br>775 | Arg | Leu | Lys | Leu |

(2) INFORMATION FOR SEQ ID NO:13:

( i ) SEQUENCE CHARACTERISTICS:
        ( A ) LENGTH: 2734 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO:13:

```
GGGCCAGTCC  GCGGGCCTTG  TCCCTATCCC  TACCAGCTAC  CCGCTTAAAA  ACTCTCTCAA        60

GGGCGTGCTT  CGACGACAGC  TCGCGCTCCT  CAACCAGGCT  TAAAGCGTCG  GCCACAACTT       120

CCTGAAAGCT  CACCCTGTAA  AACAGCTCCA  TGGACGGGGC  TTTGAGCGGG  AGTTTAAAAA       180

GGTGGTGGTG  AGGTTTATTA  GCTCTGGGTT  CGATAATCAA  GCAGGTGTTG  GTCATGATCC       240

TTGACGTTGA  TTACATCACA  GAGGACGGAA  AGCCCGTCAT  CAGGGTCTTC  AAGAAGGATA       300

AAGGAGAGTT  CAAAATTGAG  TACGACAGAG  AATTCGAGCC  CTACATCTAT  GCTCTTCTCA       360
```

```
GGGACGACTC  TGCCATCGAA  GAAATCGAAA  AGATAACCGC  AGAGAGGCAC  GGCAAGGTCG    420
TTAAGGTTAA  GCGCGCGGAG  AAGGTGAAGA  AAAAGTTCCT  CGGCAGGTCT  GTGGAGGTCT    480
GGGTCCTCTA  CTTCACGCAC  CCGCAGGACG  TTCCGGCAAT  CCGCCCGGAC  AAAATAAGGA    540
AGCACCCCGC  GGTCATCGAC  ATCTACGAGT  ACGACATACC  CTTTGCCAAG  CGATATCTCA    600
TAGACAAGGG  CTTGATTCCT  ATGGAGGGCG  ATGAGGAGCT  TAAACTCATG  TCCTTCGACA    660
TCGAGACGCT  CTACCACGAG  GGAGAAGAGT  TCGGAACCGG  GCCGATTCTG  ATGATAAGCT    720
ACGCAGATGA  AAGCGAGGCG  CGTGTGATAA  CCTGGAAGAA  GATCGACCTG  CCCTACGTCG    780
ACGTTGTCTC  CACCGAGAAG  GAGATGATAA  AGCGCTTCCT  TAAGGTCGTT  AAGGAGAAGG    840
ACCCGGACGT  GCTGATAACA  TACGACGGCG  ACAACTTCGA  CTTCGCCTAC  CTCAAAAAGC    900
GGTGTGAGAA  GCTTGGCGTG  AGCTTTACCC  TCGGCAGGGA  CGGGAGCGAG  CCGAAGATAC    960
AGCGCATGGG  CGACCGCTTC  GCCGTTGAGG  TGAAGGGCAG  GATCCACTTC  GACCTGTACC   1020
CCGCCATAAG  GCGCACCATA  AACCTCCCGA  CCTACACCCT  TGAGGCTGTA  TACGAGGCGG   1080
TTTTCGGCAA  GCCCAAGGAG  AAGGTCTACG  CCGAGGAGAT  AGCCACCGCT  TGGGAGACCG   1140
GTGAGGGGCT  TGAGGGGGTC  GCGCGCTACT  CGATGGAGGA  CGCGAGGGTT  ACCTACGAGC   1200
TTGGCAGGGA  GTTCTTCCCG  ATGGAGGCCC  AGCTTTCCAG  GCTCATCGGC  CAGGGTCTCT   1260
GGGACGTTTC  CCGCTCCAGC  ACCGGCAACC  TTGTTGAGTG  GTTTTTGCTC  AGGAAAGCCT   1320
ACGAGAGGAA  CGAACTCGCT  CCCAACAAGC  CCGACGAGAG  GGAGCTGGCG  AGGAGAAGGG   1380
GGGGCTACGC  CGGTGGCTAC  GTCAAGGAGC  CGGAGCGGGG  ACTGTGGGAT  AATATTGTGT   1440
ACCTCGATTT  TCGCTCGCTG  TACCCCTCCA  TTATCATCAC  CCACAACGTC  TCGCCAGATA   1500
CGCTCAACCG  CGAGGGATGT  AAGAGCTACG  ACGTTGCCCC  GCAGGTCGGT  CACAAGTTCT   1560
GCAAAGACTT  CCCCGGCTTC  ATTCCGAGCC  TGCTCGGAAA  CCTGCTGGAG  GAGAGGCAGA   1620
AGATAAAGAG  GAAGATGAAG  GCAACGCTCG  ACCCGCTGGA  GAGGAAGCTT  CTCGATTATC   1680
GCCAGCGCGC  TATCAAAATC  CTGGCGAACA  GCTTCTACGG  CTATTACGGC  TACGCCAGGG   1740
CAAGATGGTA  CTGCAAGGAG  TGCGCCGAGA  GCGTTACGGC  ATGGGGCAGG  GAGTACATCG   1800
AAATGGTTAT  CAGAGAGCTT  GAGGAAAAGT  TCGGTTTTAA  AGACCTCTAT  GCAGACACAG   1860
ACGGTCTTCA  TGCCACCATT  CCTGGAGCGG  ACCGTGAAAC  AGTCAAGAAA  AAGGACCTGG   1920
AGTTCTTAAA  CTATATCAAT  CCCAAACTGC  CCGGCCTTCT  CGAACTCGAA  TACGAGGGCT   1980
TCTACTCGAG  GGGCTTCTTC  GTCACCAAGA  AGAAGTACGC  GGTTATAGAC  GAGGAGGGCA   2040
AGATAACCAC  GCGCGGGCTT  GAGATAGTTA  GGAGGGACTG  GAGCGAGATA  GCGAAGGAGA   2100
CGCTGGCGAG  GGTTCTTGAG  GCGATACTCA  GGCACGGTGA  CGTTGAGGAG  GCCGTCAGAA   2160
TCGTCAAGGA  AGAGACGGAA  AAGCTGAGCA  AGTACGAGGT  TCCGCCGGAG  AAGCTGGTTA   2220
TCACCGAGCA  GATAACGCGC  GAGCTCAAAG  ACTACAAGGC  CACCGGCCCG  CACGTGGCCA   2280
TAGCGAAGCG  CCTCGCCGCG  AGGGGAATAA  AGATACGCCC  CGGGACGGTG  ATAAGCTACA   2340
TCGTCCTCAA  GGGCTCGGGG  AGAATAGGCG  ACAGGGCCAT  TCCCTTCGAC  GAGTTCGATC   2400
CGACGAAGCA  CAGGTACGAC  GCTGACTACT  ACATCGAGAA  CCAGGTTCTT  CCAGCGGTGG   2460
AGAGAATCCT  CAGGGCCTTC  GGCTACAAGA  AGGAAGACCT  GCGCTACCAG  AAGACGAGGC   2520
AGGTTGGGCT  TGGCGCGTGG  CTCGGAATGG  GAGGAGAAAG  ACTTAAACTT  TAGGAATCAT   2580
CTTTGCTCCT  ATTGTTTTTA  TACTTTATAC  TGTTTAGATC  GCTTTCTAAT  AGTTTCACCA   2640
CTGGATTGTC  TGGTCCAGTT  TTGTATTTCA  AGAGGGTTAT  GATATCCTCC  CCATAGTTTC   2700
TAATCAGATA  CATGTATAGC  TTGTAGTGGT  TCTT                                 2734
```